United States Patent [19]

Domb et al.

[11] Patent Number: 5,019,379

[45] Date of Patent: May 28, 1991

[54] UNSATURATED POLYANHYDRIDES

[75] Inventors: Abraham J. Domb, Brookline; Robert S. Langer, Somerville, both of Mass.

[73] Assignee: Massachusetts Institute of Technology, Cambridge, Mass.

[21] Appl. No.: 80,090

[22] Filed: Jul. 31, 1987

[51] Int. Cl.$^5$ .................... A61M 3/00; A61K 31/74
[52] U.S. Cl. .................... 424/78; 528/272; 523/116; 522/162; 525/418
[58] Field of Search .................... 424/78; 523/116; 528/272; 522/162; 525/418

[56] References Cited

U.S. PATENT DOCUMENTS

| | | | |
|---|---|---|---|
| 2,071,250 | 2/1937 | Carothers | 260/106 |
| 2,071,251 | 2/1937 | Carothers | 18/54 |
| 2,960,493 | 11/1960 | Conix | 260/47 |
| 3,526,612 | 9/1970 | Allphin | 260/78.4 |
| 3,981,303 | 9/1976 | Higuchi | 128/260 |
| 3,986,510 | 10/1976 | Higuchi | 128/260 |
| 4,888,176 | 12/1987 | Langer et al. | 424/78 |
| 4,888,413 | 12/1989 | Domb | 424/78 |
| 4,906,474 | 3/1990 | Langer et al. | 424/78 |

FOREIGN PATENT DOCUMENTS

| | | |
|---|---|---|
| 684685 | 4/1964 | Canada . |
| 1232684 | 1/1967 | Fed. Rep. of Germany . |
| 838986 | 6/1960 | United Kingdom . |
| 0840846 | 7/1960 | United Kingdom . |
| 840847 | 7/1960 | United Kingdom . |
| 968715 | 8/1962 | United Kingdom . |

OTHER PUBLICATIONS

Encylopedia of Poly Science, John Wiley & Sons, pp. 630–653, vol. 10.
Yoda, et al., *Bull. Chem. Soc. Jpn.*, 32, 1120 (1959).
Leong, et al., *J. Biomed. Mater. Res.* 19, 941–955 (1985).
Leong, et al., *J. Biomed. Mater. Res.* 20, 51–64 (1986).
Hill and Carothers, Studies of Polymerization and Ring Formation XIV, A Linear Superpolyanhydride and a Cyclic Dimeric Anhydride from Sebacic Acid, *J. Amer. Chem. Soc.*, 54, 1969 (1932).
Leong, et al., *Macromolecules*, 20(40, 705 (1987).
Rosen, et al., *Biomaterials* 4, 131 (1983).
Shopor, et al., *Chem. Abst.* 71, 91956w (1969).
Ibay, et al., Synthesis and Properties of Polymers for Biodegradable Implants, 505–509.
Wise, et al., Evaluation of Repair Materials for Avulsive Combat Type Maxillofacial Injuries, CRC *Biopolymer Controlled Release Systems*, vol. 11, 170–186 (1984).
Yoda, Synthesis of Polyanhydrides XI Synthesis and Properties of New Polythioetherpolyanhydrides, *Makromol. Chem.*, p. 36 (1962).
Polyanhydrides, *Ency. of Poly Sci. & Tech.*, 10, 630, 1969.
Yoda, Synthesis of Polyanhydrides XII, Crystalline and High Melting Polyamidepolyanhydride of Methylenebis-(p-Carobxyphenyl)amide, *Journal of Polymer Science*, Part A, vol. 1 1323 (1963).
Yoda, Synthesis of Polyanhydrides X, Mixed Anhydrides of Aromatic and Five-Membered Heterocyclic Dibasic Acids, *Makromol. Chem.* 10 (1962).
A. Conix, Poly [1,3-bis (p–carboxyphenoxy)–propane anhydride], Macromolecular Synthesis, vol. Two, 95 (1966).
Hill and Carothers, Studies of Polymerization and Ring Formation XIX, Many-Membered Cyclic Anhydrides, *J. Amer. Chem. Soc.* 55, 5023 (1933).

*Primary Examiner*—Thurman Page
*Assistant Examiner*—Peter F. Kulkosky
*Attorney, Agent, or Firm*—Kilpatrick & Cody

[57] ABSTRACT

A class of unsaturated polyanhydrides having double bonds available for secondary polymerization is disclosed. A crosslinked material having improved or different physical and mechanical properties can be prepared from these polyanhydrides, via secondary polymerization. The synthesis and characteristics of one unsaturated polyanhydride based on fumaric acid and its copolymers with aliphatic and aromatic diacids, prepared by either the melt-polycondensation method or by solution polymerization, is described in detail.

These polymers are well suited for use in controlled release drug delivery devices. The polymers can also be used as a bioerodible bone cement where the polymer is first cast as a solution onto a bone fracture and then crosslinked by radiation or radical polymerization to yield a strong, adhesive material.

15 Claims, 3 Drawing Sheets

UNSATURATED POLYANHYDRIDES

BACKGROUND OF THE INVENTION

The present invention is in the general area of polymers for biomedical application and in particular is a group of unsaturated polyanhydrides having a double bond available for secondary polymerization.

A number of polymers have been used in biomedical applications including polyanhydrides, polyorthoesters, polylactic acid, and polyvinylacetate. One of the advantages of polyanhydrides in these applications is that they are both biodegradeable and biocompatible.

One major application is in biodegradable controlled release systems. These devices obviate the need to surgically remove the drug-depleted device. Biodegradable matrix systems also enjoy a number of other advantages in terms of simplicity in design and predictability of release if the release is controlled solely by the degradation of the matrix. In many cases, however, the release is augmented by diffusion though the matrix, rendering the process difficult to control. This is particularly true if the matrix is hydrophilic and therefore absorbs water, promoting degradation within the interior of the matrix. To maximize control over the release process, it is desirable to have a polymeric system which degrades only from the surface and deters the permeation of the drug molecules. Achieving such a heterogeneous degradation requires the rate of hydrolytic degradation on the surface to be much faster than the rate of water penetration into the bulk. Accordingly, the ideal polymer has a hydrophobic backbone in combination with a water labile linkage.

Polyanhydrides were initially proposed by Hill and Carouthers in the 1930's to be a substitute for polyesters in textile applications. The idea was later rejected because of their hydrolytic instability. However, it is this property that renders polyanhydrides appealing for controlled-release applications.

Aromatic and aliphatic polyanhydrides were first synthesized in 1909 and 1932, respectively. The methods most commonly used were melt-polycondensation methods. (Yoda, et al., *Bull. Chem. Soc. Jpn.*, 32, 1120 (1959)). The materials used in textile applications, while useful, can provoke an inflammatory response when used in vivo for medical applications. Further, their release characteristics are not always uniform.

Characterization of the degradation and release characteristics, and the biocompatibility and chemical reactivity, of polyanhydrides as drug-carrier matrices was reported by Leong, et al., in *J. Biomed. Matter. Res.*, 19, 941–955 (1985) and 20, 51–64 (1986). The polyanhydrides used by Leong et al are vastly improved over the polyanhydrides first prepared for use in textiles. These studies indicate that the method for manufacture as well as the purity of the starting materials can be improved in order to improve the in vivo response, i.e., decrease the inflammatory response and improve linear release.

Co-pending application U.S. Ser. No. 892,809 filed Aug. 1, 1986 by Abraham J. Domb and Robert S. Langer entitled "Synthesis and Application of High Molecular Weight Polyanhydrides" discloses one approach to overcoming the deficiencies in both the mechanical and physical properties of the polymers as well as the in vivo response. Their method is to synthesize high molecular weight polyanhydrides from extremely pure diacids and isolated prepolymers under optimized reaction conditions. High molecular weight polyanhydrides were defined as having an intrinsic viscosity of greater than 0.3 dl/g in chloroform at 23° C. and a weight average molecular weight of greater than 20,000.

It is important for drug-delivery applications to have polymers having good solubility, required for film casting or microencapsulation, as well as stability both in solution and in the solid state. Studies of the stability of polyanhydrides in solution and in solid state have demonstrated that linear polyanhydrides tend to depolymerize. Aromatic polyanhydrides are more stable but, unfortunately, also less soluble. If the linear polymers could be crosslinked after polymerization, their stability would not only be enhanced but new applications could be developed.

It is therefore an object of the present invention to provide cross-linkable polymers which are stable in solution yet which can be solubilized for film casting or microencapsulation.

It is another object of the present invention to provide soluble polymers having linear release when cast as controlled drug-delivery devices.

It is still another object of the present invention to provide polymers which can be cross-linked for use in biomedical applications such as in bone adhesion.

SUMMARY OF THE INVENTION

A class of unsaturated polyanhydrides having double bonds available for secondary polymerization is disclosed. A crosslinked material having improved or different physical and mechanical properties can be prepared from these polyanhydrides, via secondary polymerization. The synthesis and characteristics of one unsaturated polyanhydride based on fumaric acid and its copolymers with aliphatic and aromatic diacids, prepared by either the melt-polycondensaticn method or by solution polymerization, is described in detail.

These polymers are well suited for use in controlled release drug delivery devices. The polymer (with or without bioactive agents) is first cast as a film or microcapsule which has double bonds available for crosslinking by irradiation or using radical salt polymerization. The degradation profile and the release characteristics are more uniform than with other polymers since crosslinking helps prevent diffusion of water into the material. The degree of crystallinity also appears to play an important role in preventing water diffusion into the polymer bulk and thereby prevents bulk erosion.

The polymers can also be used as a bioerodible bone cement where the polymer is first cast as a solution onto a bone fracture and then crosslinked by radiation or radical polymerization to yield a strong, adhesive material.

DETAILED DESCRIPTION OF THE INVENTION

Figure 1:
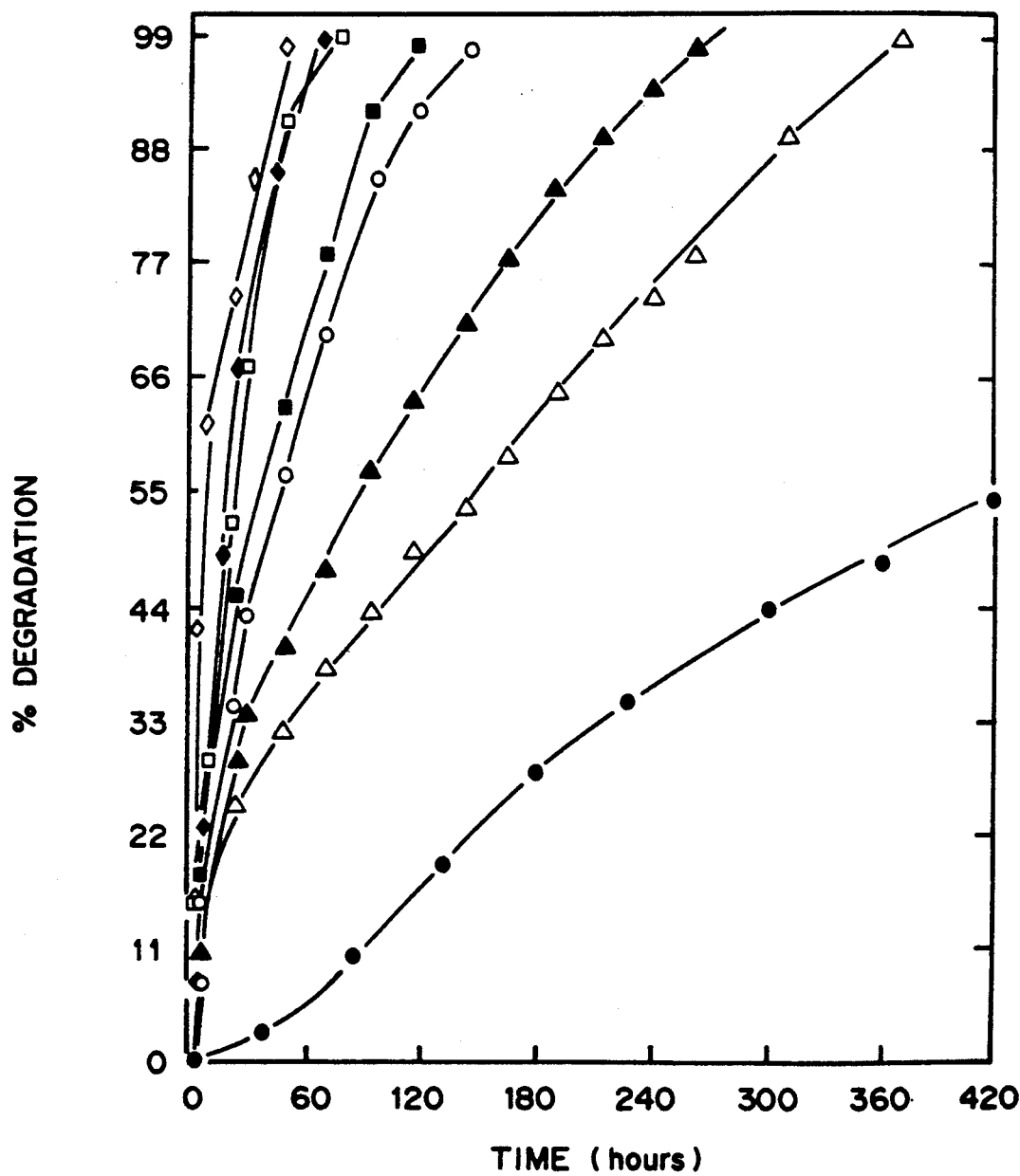
FIG. 1 is a graph of the hydrolytic degradation of p(FA), percent degradation versus time (hours), comparing degradation in phosphate buffer-THF and phosphate buffer alone as a function of pH.

A class of polyanhydrides for use in biomedical application has been developed consisting of unsaturated polyanhydrides having double bonds available for secondary polymerization. Other useful polymers include copolymers of 1,4-phenylenediacrylic acid with aromatic and aliphatic diacids.

Polyfumaric acid, (p(FA)), and copolymers of fumaric acid were prepared to demonstrate the synthesis and characteristics of unsaturated polyanhydrides.

Polyfumaric acid is prepared either by melt-polycondensation or by solution polymerization. In the melt polymerization, a mixed anhydride of acetic acid and fumaric acid is polymerized at between 120° C. and 180° C. for 30 minutes under vacuum. The fumaric acid mixed anhydrides are preferably polymerized at 180° C. under vacuum using an acetone dry ice trap. The melted prepolymer solidifies after 10 minutes of polymerization at this temperature.

The preferred methods of solution polymerization of polyanhydrides is described by Leong, et al, in *Macromolecules* 20(4), 705 (1987) and by Domb et al in copending application U.S. Ser. No. 080,332 filed July 31, 1988 entitled "One Step Polymerization of Polyanhydrides now U.S. Pat. No. 4,906,474. This method allows polymerization of heat sensitive copolymers of fumaric acid or the incorporation of heat sensitive materials into the polyanhydride as it is polymerized.

The properties of fumaric acid polyanhydrides formed by melt polymerization are shown in Table I. The properties of fumaric acid polyanhydrides formed by solution polymerization are shown in Table II (using a dehydrative coupling agent, phosgene or diphosgene) and Table III (polymerized in chloroform using an acid chloride dehydrochlorination coupling agent for 24 hours at room temperature with a ratio of acid: acid chloride:amine of 1:1:2.2).

These methods are described in greater details in the examples.

TABLE I

Fumaric Acid Polyanhydrides[a]
Prepared by Melt Polymerization

| Polymer[b] | Molecular Weight Mw. | Molecular Weight Mn. | [η] (dl/g) | Melt. Point (°C.) |
|---|---|---|---|---|
| pFA | — | — | — | 248 |
| p(FA:SA) (93:7) | — | — | — | 198 |
| p(FA:SA) (70:30) | 18,500 | 10,600 | 0.28 | 148 |
| p(FA:SA) (50:50) | 20,900 | 9,100 | 0.31 | 99 |
| p(FA:SA) (19:81) | 29,350 | 13,250 | 0.42 | 70 |

[a]Polymerized at 180° C. Mw was determined by GPC. Viscosity was measured in CHCl$_3$ at 23° C.
[b]FA - fumaric acid, SA - sebacic acid, DD - dodecanedioic acid, AA - adipic acid.

TABLE II

Fumaric Acid Polyanhydrides.
Prepared by Dehydrative Solution Polymerization[a]

| Acid[b] | Coupling Agent | Acid Acceptor | Molecular Weight Mw. | Molecular Weight Mn. | Melting Point (°C.) |
|---|---|---|---|---|---|
| FA | Phosgene | TEA | — | — | 245 |
| FA | Phosgene | Pyridine | — | — | 248 |
| FA | Diphosgene | TEA | — | — | 245 |
| FA:SA | Phosgene | TEA | 5300 | 3400 | 91 |
| FA:SA | Phosgene | PVP | 4900 | 2990 | 91 |
| FA:SA | Diphosgene | TEA | 5100 | 3450 | 90 |
| FA:SA | Diphosgene | PVP | 5840 | 3010 | 92 |

TABLE II-continued

Fumaric Acid Polyanhydrides.
Prepared by Dehydrative Solution Polymerization[a]

| Acid[b] | Coupling Agent | Acid Acceptor | Molecular Weight Mw. | Molecular Weight Mn. | Melting Point (°C.) |
|---|---|---|---|---|---|
| FA:SA | Diphosgene | K$_2$CO$_3$ | 2850 | 1910 | 91 |

[a]Polymerized in CHCl$_3$ at 25° C.
[b]FA - fumaric acid, SA - sebacic acid, TEA - triethylamine, PVP - poly(4-vinylpyridine).
[c]Mw was determined by GPC.

TABLE III

Fumeric Acid Polyanhydrides
Prepared by Dehydrochlorination Solution Polymerization

| Acid | Acid Chloride | Acid Acceptor | Molecular Weight[b] Mw | Molecular Weight[b] Mw | Mp[c] (°C.) | Yield[c] (%) |
|---|---|---|---|---|---|---|
| SA | SA | TEA | 16700 | 7650 | 76 | 63 |
| FA | SA | TEA | 5800 | 3250 | 9095 | 60 |
| FA | SA | Pyridine | 5100 | 3100 | 90–96 | 65 |
| FA | SA | PVP | 5900 | 3600 | 92–96 | 70 |
| SA | FA | TEA | 5500 | 3800 | 90–95 | 60 |
| SA | FA | PVP | 5900 | 3500 | 94–95 | 62 |
| FA | AA | TEA | 4600 | 2950 | d | 54 |
| DD | FA | TEA | 5700 | 4100 | 95–98 | 60 |
| FA | AA | PVP | 4200 | 2550 | d | 56 |
| DD | FA | PVP | 4900 | 2800 | 95–98 | 45 |
| FA | FA | TEA | — | — | 248–250 | 85 |

[a]polymerized at room temperature for 24 hours in chloroform of acid; acid chloride:amine 1:1:2.2 Molar ratio.
[b]Molecular weight of purified polymers was determined by GPC.
[c]determined on the purified polymer.
[d]undefined melting point.

Unfortunately, the crystalline fumaric acid homopolymer is insoluble in common organic solvents and has poor mechanical properties and is therefore not useful for drug delivery applications. However, copolymerization of fumaric acid with aliphatic diacids produces soluble polymers with weight average molecular weights between 18,500 and 29,350. A number of factors influence the properties and molecular weight of the polymers, including selection of the monomers, the ratio of the monomers to each other, and the polymerization conditions. For example, when polymerized by melt condensation, reaction times must be limited to 30 minutes or less at 180° C. to avoid the formation of insoluble polymers. The melting points of the copolymers decrease with increasing concentrations of the aliphatic comonomer. Increasing the ratio of a monomer such as sebacic acid, (SA) yields higher molecular weight polymers. All copolymers possess film-forming properties when cast from chloroform solutions at low temperatures.

The melting points, molecular weights, and IR of the fumaric acid copolymers are shown in Table IV.

TABLE IV

Fumaric Acid Copolymers
Synthesized by Melt Polycondensation

| Polymer[c] | Melting Point (°C.) | Molecular Weight[a] Mw | Molecular Weight[a] Mn | IR[b] (cm$^{-1}$) |
|---|---|---|---|---|
| p(FA:AA) (1:1) | d | 17,000 | 7,800 | 1800,1725,3080 |
| p(FA:DD) (1:1) | 98 | 28,100 | 12,950 | 1800,1725,3080 |
| p(FA:CPP) (1:1) | 110 | e | e | 1780,1725,1600 |
| p(FA:CPP:SA) (1:1:0.25) | 150 | 19,450 | 8,590 | 1600,1780,1730, 3080 |
| p(FA:CPP:SA) (1:1:1) | 95–98 | 20,100 | 9,110 | 1,600,1780,1730, 3080 |
| p(FA:IP) (1:1) | d | f | f | 1790,1730,1600 |
| p(FA:SA:IP) (1:1:1) | d | 16,910 | 7,850 | 1800,1730,1600, |

TABLE IV-continued

Fumaric Acid Copolymers Synthesized by Melt Polycondensation

| Polymer[c] | Melting Point (°C.) | Molecular Weight[a] Mw | Mn | IR[b] (cm$^{-1}$) |
|---|---|---|---|---|
| | | | | 3080 |

[a] Molecular weight was determined by GPC.
[b] Characteristic IR for anhydride carboxyls (1730, 1780, 1800 cm$^{-1}$), olefinic protons (3080 cm$^{-1}$) and aromatic ring (1600 cm$^{-1}$).
[c] FA - fumaric acid, AA - adipic acid, DD - dodecanedioic acid, CPP - 1,3-bis(p-carboxyphenoxypropane), SA - sebacic acid, IP - isophthalic acid.
[d] Undefined melting point. Polymers are soft at room temperature and turns into a liquid at 75-80° C. for p(FA:SA), 55-60° C. for p(FA:SA:IP) (1:1:1), and 105-110° C. for p(FA:IP).
[e] The polymer after 30 min. polymerization is not soluble in common organic solvents. Soluble polymer, after 10 min. reaction, shows molecular weight of 5250 and 2950 for Mw and Mn respectively.
[f] Same as e. Soluble polymer had molecular weights 4800 and 2320 for Mw and Mn, respectively.

The polymers described in Tables I, II, III, and IV were characterized by infrared spectroscopy performed on a Perkin-Elmer 1430 spectrophotometer (Perkin-Elmer, Mass). Polymeric samples were film cast onto NaCl plates from solutions of the polymer in chloroform. Prepolymer samples or insoluble polymers were either pressed into KBr pellets or dispersed in nujol onto NaCl plates. The melting points of prepolymers and polymers were determined on a Fisher-Johns melting point apparatus. The molecular weights of the polymers and prepolymers were estimated on a Perkin-Elmer GPC system (Perkin-Elmer, Mass) consisting of a series 10 pump and 3600 data station with the LKB 214-rapid spectral detector at 254 nm wavelength. Samples were eluted in chloroform through two PL Gel columns (Polymer Laboratories) 100 A and 1000 A pore sizes) in series at flow rates of 1.5 ml/min. Molecular weights of polymers were determined relative to polystyrene standards (Polysciences, PA., molecular weight range 500 to 1,500,000) using CHROM 2 and GPC 4 computer programs (Perkin-Elmer, Mass). Wide-angle X-ray diffraction of polymers in the form of pressed disks, 1 mm thick, was recorded on a Phillips X-ray diffractometer using a nickel-filtered CuK source. 'H-NMR spectra were obtained with a Varian 250 MHz NMR spectrometer using deuterated chloroform as solvent and tetramethylsilane (TMS) as an internal reference. UV measurements were performed on a Perkin-Elmer 553 UV/Vis spectrophotometer. Elemental analysis were performed by Galbraith Laboratories, Knoxville, Tennessee.

EXAMPLE 1 PREPARATION OF FUMARIC ACID POLYANHYDRIDES BY MELT-CONDENSATION

Prepolymers were prepared as follows. The mixed anhydride of sebacic acid and dodecanedioic acid with acetic acid were prepared as described by Domb, A., et al, *J. Polymer Science* (1987, in press) and Rosen, et al., *Biomaterials* 4, 131 (1983). Fumaric acid prepolymer was prepared by adding 40 g (0.34 mole) of fumaric acid to 500 ml refluxing acetic anhydride. The reaction was continued for five hours. The clear yellow-brown solution was left to crystallize at −20° C. for three days. The white crystalline precipitate was then filtered and washed with dry ether to yield 25 g (45% yield). The melting point of the prepolymer was 75° C, IR (KBr, pelat, cm$^{-1}$)$\nu_{C=C}$ 3070 (sharp), $\nu_{anhydride}$ 1800, 1735. 'H-NMR (CDC13, ppm) 6.92 (s,2H), 2.32 (s,6H).

A solution of 22 mmole acetyl chloride (1.6 ml in 10 ml chloroform) was added to a stirring mixture of 1.16 g (10 mmole) sebacic acid and 2.5 g (22 mmole) poly(4-vinylpyridine) (PVP) in 15 ml chloroform immersed in an ice water bath. The reaction was continued overnight at room temperature. The mixture was then filtered and the filtrate evaporated to dryness. Excess acetyl chloride was removed by vacuum over 24 hours. The residue was washed with diethylether: petroleum ether (1:1). 1.5 g was recovered (80% yield). The prepolymer had a melting point of 70° C., IR (KBr, pelat, cm$^1$) anhydride 1800, 1740 'H-NMR (CDCl$_{13}$, ppm) 6.92 (s,2H), 2.32 (s,6H).

The prepolymers underwent melt polycondensation as follows. In a typical reaction, 4.0 g (0.034 mole) fumaric acid prepolymer was placed in a glass tube with a side arm and polymerized at 180° C. under vacuum of less than 100 microns with an acetone/dry ice trap to collect the acetic anhydride formed in the polymerization. After ten minutes the melt turned to a creamy solid. Polymerization was stopped at 30 minutes. The creamy solid was ground to powder and washed with dry ether to yield 1.8 grams (95%). The polymer melting point was 248-249° C. with some decomposition. Elemental analysis: C —48.45, H—2.11 (calculated C —48.98, H—2.0).

Copolymers were similarly prepared by polymerizing a mixture of prepolymers at 180° C. under vacuum. In a typical study, 2.0 g (10 mmole) fumaric acid (FA) prepolymer was mixed with 2.3 g (10 mmole) sebacic acid (SA) prepolymer and polymerized at 180° C. under 100 microns vacuum for 25 minutes. The crude copolymers were dissolved in methylene chloride or chloroform (10 g polymer in 50 ml organic solution) and poured dropwise into 500 ml stirring petroleum ether. The light tan precipitate was separated by filtration, washed with diethylether and dried in a vacuum oven at 35° C. for 24 hours.

EXAMPLE 2 SOLUTION POLYMERIZATION OF FUMARIC ACID POLYANHYDRIDES

Methods for solution polymerization of polyanhydrides are reported by Leong et al. in Macromolecules 20(4), 705-712 and Shopor et al. *Chem. Abst.* 76, 91956w (1969). The following method is described by Domb, et al. in co-pending application entitled "One Step Polymerization of Polyanhydrides" filed on July 30, 1987.

One equivalent coupling agent was added dropwise to a stirring solution of 1 eq. dicarboxylic acids and 2.5 eq. base in chloroform. The reaction mixture was stirred at 25° C. for 3 hours. When either poly(4-vinylpyridine) (PVP) or K$_2$CO$_3$ was used as the acid acceptor, the insoluble solids (e.g., PVP.HCL, KCl) were removed by filtration. The filtrate was quenched in excess petroleum ether. The precipitated polymer was isolated by filtration and dried in a vacuum oven at 40° C. for 24 hours. When either triethylamine (TEA) or pyridine were used, the polymerization mixture was quenched in petroleum ether. The precipitated polymer was redissolved in chloroform and washed rapidly with cold water, pH 6.0. The chloroform solution was dried over MgSO$_4$, and quenched a second time in petroleum ether.

Insoluble polyanhydrides, pFA or poly(fumaric-sebacic) anhydride (p(FA:SA))(93:7), were polymerized as above, but with only soluble amines (TEA or pyridine), as the acid acceptors. The polymer precipitated during the polymerization and was isolated by filtration.

Polymerization of fumaric acid and its copolymers with sebacic acid shows similar results whether polymerization is with a coupling agent such as phosgene or diphosgene or an acid-acid chloride polymerization reaction. For either reaction, soluble or insoluble bases are suitable as acid acceptors.

In a typical example, 0.5 g (0.5 eq.) diphosgene (the coupling agent) was added dropwise into a stirring mixture of 1.01 g (0.5 eq.) sebacic acid, 0.58 g, (0.5 eq.), fumaric acid and 3 g (2.5 eq.) PVP in 20 ml chloroform. After 3 hours at 25° C., the insoluble PVP.HCL was removed by filtration. The filtrate was quenched in 100 ml petroleum ether, the precipitated polymer isolated by filtration, washed with anhydrous diethyl ether and dried at 40° C. for 24 hours in a vacuum oven.

PFA is highly crystalline and has poor mechanical properties. The crystalline polymer has a high melting point and is insoluble in common organic solvents. These properties make it difficult to process using solvent casting, microencapsulation techniques, and injection molding. Compression molded samples tended to crumble when immersed in an aqueous environment. Polymerization with citraconic acid was tried as a means for improving these properties. Unfortunately, a cyclic monomeric anhydride was formed using either the solution or melt polymerization methods.

IR spectra of pFA acid shows anhydride bonds at 1780 and 1740 cm$^{-1}$, characteristic of conjugated non-cyclic anhydrides, and olefinic C-H stretch at 3080 cm$^{-1}$ (sharp singlet). All copolymers revealed a characteristic IR absorbance for anhydrides at 1800 and 1735 cm$^{-1}$. The existence of double bonds, as confirmed by the spectra, are important for secondary polymerization, which can be used to produce a cross-linked matrix with improved mechanical and physical properties.

The composition and the sequence of the comonomers in p(SA:FA) can be estimated from the $^1$H-NMR spectrum. The ratio between fumaric acid and sebacic acid comonomers is determined from the ratio of the olefinic protons at 6.9 (2H, fumaric acid) and aliphatic protons at 1.34 (8H, sebacic acid). For example, for a prepolymer originally having a calculated 50:50 molar ratio, the ratio determined from $^1$H-NMR is 46:56 and for a polymer having an intended ratio of 15:85, the prepolymer showed a ratio of 17:81 by $^1$H-NMR. The sequence of the polymers was estimated as follows: the aliphatic protons (2CH$_2$) of the methylenes conjugated with the anhydride bond of sebacic acid split into two triplets, one at $\delta=2.447$ ppm (j=7.5 Hz) and one at $\delta=2.545$ ppm (j=7.5 Hz). The olefinic protons (2H) are split into two singlets, at $\delta=6.97$ and $\delta=2.447$ ppm. Both split peaks show 1:1 integration ratios. These splittings are presumably due to the type of anhydride bonds in the polymer: anhydride bonds of sebacic acid-fumaric acid ($\delta=2.545$ ppm), anhydride bonds of sebacic acid-sebacic acid ($\delta=2.447$ ppm), anhydride bonds of fumaric acid-sebacic acid ($\delta=6.91$ ppm) and anhydride bonds of fumaric acid-fumaric acid ($\delta=6.97$). $^{13}$C NMR spectra of copolymers of sebacic and fumaric acid have characteristic peaks (ppm): carboxylic carbons at 160-170, olefinic carbons at 132-136, and aliphatic carbons at 24-35.

EXAMPLE 3 PREPARATION AND CHARACTERIZATION OF POLYMERIC CONTROLLED DRUG-RELEASED DEVICES

Films were made from the polymers using 20% w/v copolymer solutions in dichloromethane cast on glass petri dishes. The dishes were placed on dry ice or stored at −20° C. to evaporate the solvent.

Hydrolytic degradation of the polymer films was performed at 37° C., either in 0.1 M phosphate buffer, pH 7.4, or in a phosphate buffer-tetrahydrafuran (PB-THF) mixture (1:1, v/v). The degradation kinetics were followed by measuring the UV absorbance at 235 nm of the periodically changed buffer solution. Disk shaped samples of 15 mm diameter and 1 mm thickness, prepared by compression molding of 200 mg polymer at 30,000 psi, were used.

The hydrolytic degradation of pFA at various pHs is shown in FIG. 1. The degradation was performed in aqueous buffer solutions and in buffer-THF mixture (1:1). Increasing acidity decreases the degradation rate, probably due to the decrease in solubility of the fumaric acid which shields and prevents the degradation of the core. However, when the degradation is performed in a medium in which the degradation products are soluble (for example, the phosphate buffer-THF mixture), rapid degradation occurs.

Figure 2:
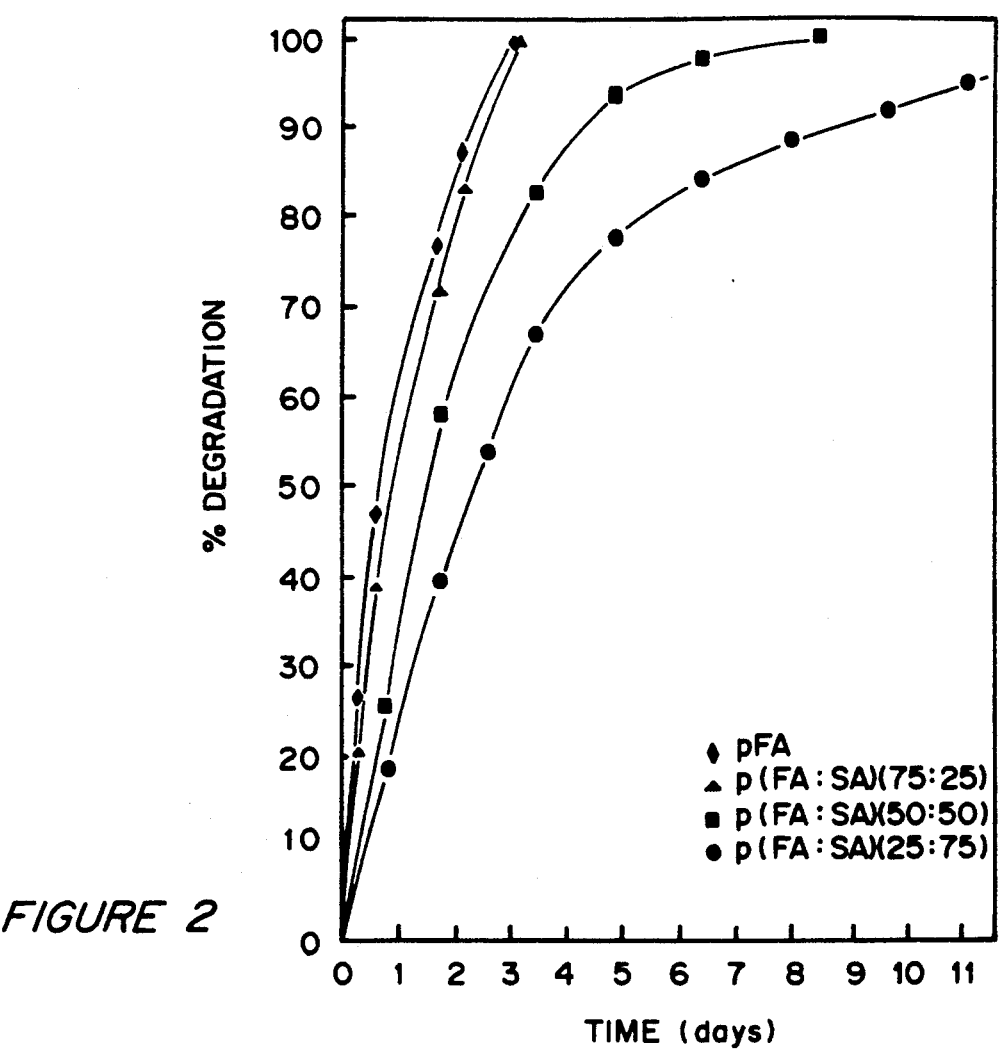
FIG. 2 is a graph of the degradation of p(FA:SA), percent degradation versus time (days).
Figure 3:
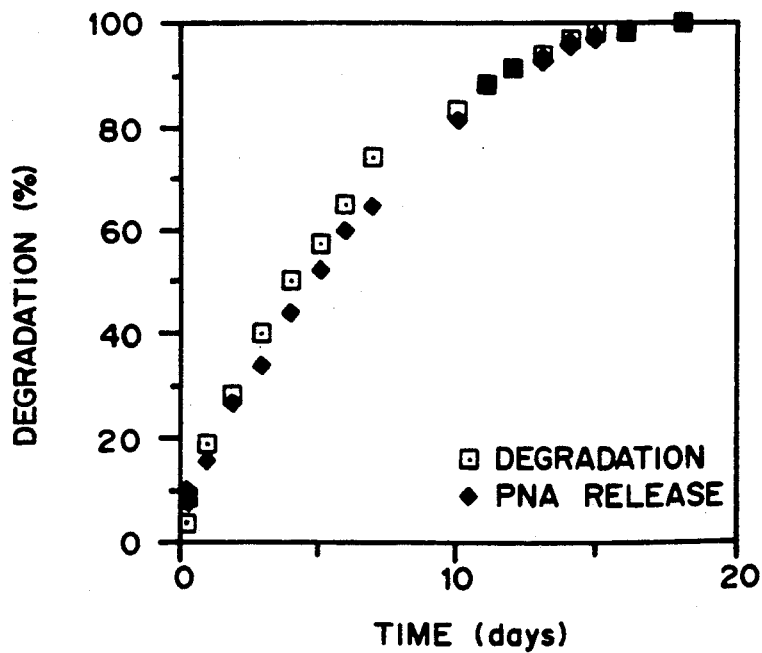
FIG. 3 is a graph of the release of PNA from (FA:SA)(1:1), percent degradation versus time (days).
Figure 4:
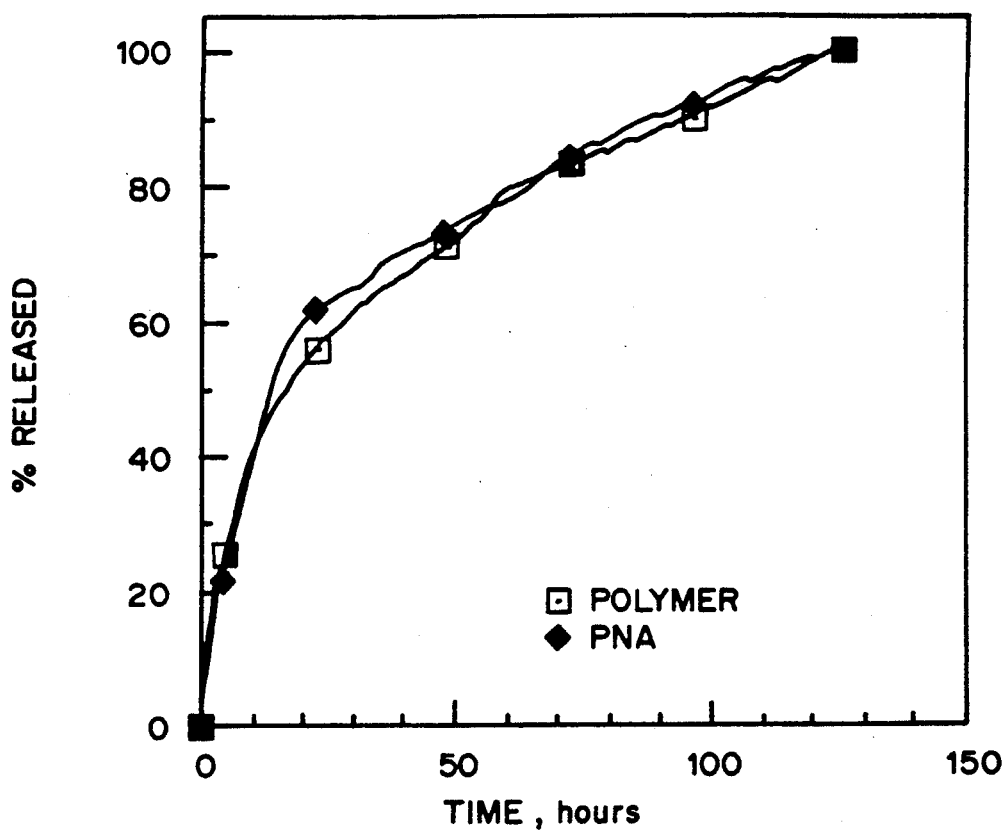
FIG. 4 is a graph of PNA released from p(FA:SA) (1:1) film, percent polymer or PNA released versus time (hours).

FIG. 2 shows the degradation of different copolymers in pH 7.4 buffer. The degradation rate varies among the polymers. pFA degrades faster than pSA. Copolymers of pFA and pSA display release rates between the rates of the homopolymers. FIGS. 3 and 4 demonstrate that the polymer degradation and release of the encapsulated compound are the same for polymers having a ratio of FA:SA of 20:80 and a ratio of FA:SA of 50:50. This is probably due to the high crystallinity of the polymers which help to prevent water from penetrating the polymer and accelerating release by diffusion. The release and degradation characteristics of the fumaric acid polymers are also shown in Table V.

TABLE V

Release and Degradation of Fumaric Acid Polymers[a]

| Polymer[b] | Degradation Rate[c] (mg/cm$^2$/h) | t½ (t)[d] (days) | PNA Release Rate[c] (mg/cm$^2$/h) | t½ (t)[d] (days) |
|---|---|---|---|---|
| p(FA:AA) (1:1) | 1.06 | 1 (3) | 0.020 | 1 (3) |
| p(FA:DD) (1:1) | 0.461 | 3 (15) | 0.011 | 3 (15) |
| p(FA:CPP) (1:1) | 0.092 | 15 (45) | 0.013 | 4 (28) |
| p(FA:CPP:SA) (1:1:0.25) | 0.085 | 14 (42) | 0.014 | 4 (27) |
| p(FA:CPP:SA) (1:1:1) | 0.107 | 13 (42) | 0.009 | 5 (28) |
| p(FA:IP) (1:1) | 0.463 | 3 (10) | 0.025 | 1 (10) |
| p(FA:SA:IP) (1:1:1) | 0.463 | 3 (10) | 0.023 | 2 (10) |

[a] Release and degradation from compression molded discs of 5% PNA in polymer (15 × 1 mm, 200 mg PNA) in phosphate buffer (0.1 M, pH 7.4) at 37° C.
[b] FA - fumaric acid, AA - adipic acid, DD - dodecanedioic acid, CPP - 1,3-bis(P-carboxyphenoxy)propane, SA - sebacic acid, IP - isophthalic acid.
[c] t½ is the time for 50% release or degradation, (t) is the time for complete release or degradation. In all polymers an initial PNA release of 15 to 20% over the first 4 hours was found.
[d] Determined from the linear part of the release or degradation vs. time, after the initial 4 hours.

The polymers display zero order release kinetics when in solution. This kind of continuous release is required for most drug delivery applications where the goal is to provide a sustained release over a predetermined period of time. For oral delivery, a release time would preferably be less than 48 hours, more preferably less than one day.

Figure 5:
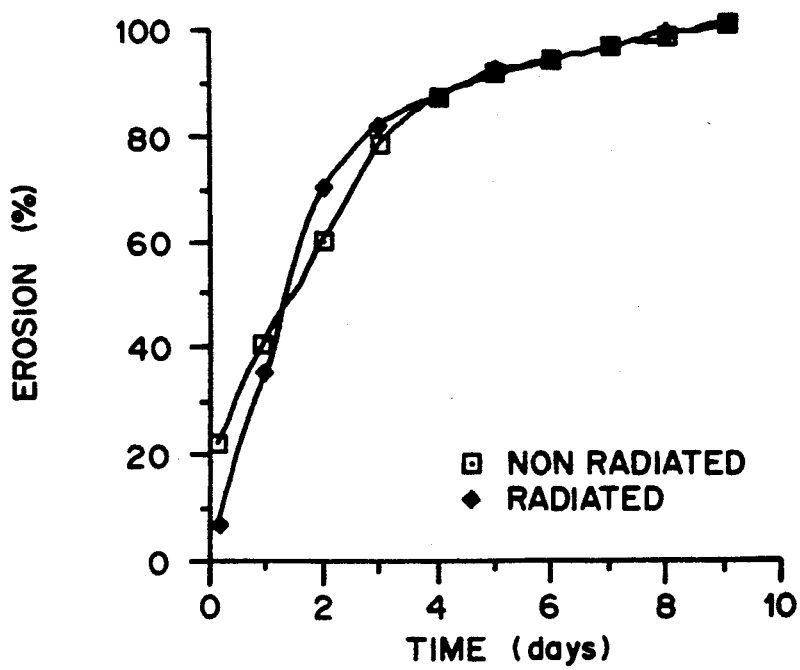
FIG. 5 is a graph of the effect of radiation on p(FA:SA) erosion, percent versus time (days).

The polymers of p(FA:SA) having ratios of 20:80 and 50:50 degrade and release the p-nitroaniline at almost the same rate. However, the rate at which 50:50 polymer degrades and releases its contents is faster than the 20:80 copolymer. The fact that the dye release is determined by the polymer erosion can be explained partially by the high crystallinity of this polymer which may help to prevent water from penetrating the polymer and thus accelerate release by diffusion. In all cases, the disk remained intact without disintegration until the end of the release study, at which time it had completely disappeared.

p(FA:SA) copolymers can be crosslinked by a number of methods. In the preferred method, the copolymers are radiated with 2 Mrad $\gamma^{60}$Co at room temperature. The advantage to this method of crosslinking is that both crosslinking and sterilization are obtained at the same time. This yields an insoluble polymer with an undefined melting point, indicating crosslinking. The polymers can also be crosslinked using benzoyl peroxide and an accellerator, a method known to those skilled in the art. FIG. 5 graphs the degradation of p(FA:SA) (1:1) before and after irradiation. The results show that gamma irradiation does not alter the rate of degradation although degradation was slightly more uniform.

An advantage of having polymeric drug-delivery devices of this composition with rapid degradation properties is that they are ideal for use in oral drug delivery. It is desirable both to have a rapid delivery rate as well as pH dependency of the drug release for oral release.

With respect of the structure of the polymers, the fraction of crystallites is estimated by X-ray diffraction. The crystallinity is determined by the equation $$Xc = \frac{Ac}{Aa + Ac},$$

where Xc is the percent crystallinity of the homo or copolymers, Aa is the area under the amorphous hump and Ac is the area remaining under the crystalline peaks. When two monomers both forming a semi-crystalline homopolymer are polymerized, the degree of copolymer crystallinity decreases as the second constituent is added to either homopolymer. Degree of crystallinity appears to play an important role in preventing water diffusion into the polymer bulk and thereby prevents bulk erosion. Since an application of these polymers is in a drug-delivery system, the high crystallinity of these polymers may be an asset.

As discussed by Ibay, et al., "Synthesis and Properties of Polymers for Biodegradable Implants", 505–509, and "Evaluation of Repair Materials for Avulsive Combat-type Maxillofacial Injuries" Wise, et al., *CRC Biopolymer Controlled Release Systems*, vol. II 170–186, (1984) a number of materials have been used as biocompatible, biodegradable materials for the temporary replacement and/or repair of bone. The material described by Wise and Ibay et al., is a composition containing poly(propylene fumerate), vinylpyrollidone, an inert filler such as calcium sulfate and benzoyl peroxide. The present invention provides an alternative material for use as an adhesive or filler in bone repair. One of the clear advantages of the material of the present invention is that it may applied by a solution and then polymerized by irradiation or using radical polymerization with a catalyst, for example, one of the peroxides such as Benzoyl peroxide, using N,N - Dimethyl - p - toludine (DMT) as an accelerator.

Although the present invention has been described with reference to specific embodiments, any unsaturated polyanhydride with double bonds which can be subjected to secondary polymerization for use in biomedical applications is believed to be encompassed by the present invention. Not only useful for controlled drug delivery, these polymers can be used as a bone cement where polymerization is initiated either by the presence of a catalyst or by gamma irradiation. Other applications will be apparent from the foregoing description.

Variations and modifications of the present invention, unsaturated polyanhydrides for use in biomedical applications, will be obvious to those skilled in the art of organic synthesis. Such modifications and variations are intended to come within the scope of the appended claims.

We claim:

1. An unsaturated polyanhydride copolymer of aliphatic and aromatic dicarboxylic acids and a diacid selected from the group consisting of fumaric acid and 1,4-phenylenediacrylic acid having at least one double bond available for crosslinking, wherein said polyanhydride has a melting point of less than about 200° C. and a high degree of crystallinity and is soluble in organic solvents.

2. The polyanhydride of claim 1 wherein said polyanhydride is synthesized by reacting fumaric acid or 1,4-phenylenediacrylic acid with acetic anhydride and polymerizing by melt polycondensation.

3. The polyanhydride of claim 1 wherein said polyanhydride is synthesized by reacting fumaric acid or 1,4-phenylenediacrylic acid with a dehydrochlorination coupling agent and an insoluble acid acceptor.

4. The polyanhydride of claim 1 wherein said polyanhydride is synthesized by reacting fumaric acid or 1,4-phenylenediacrylic acid with a dehydrative coupling agent and an acid acceptor.

5. A drug delivery device comprising an unsaturated polyanhydride copolymer of aliphatic and aromatic dicarboxylic acids and a diacid selected from the group consisting of fumaric acid and 1,4-phenylenediacrylic acid having at least one double bond available for crosslinking, wherein said polyanhydride has a melting point of less than about 200° C. and a high degree of crystallinity and is soluble in organic solvents, and a bioactive compound.

6. The drug delivery device of claim 5 wherein said polyanhydride is crosslinked.

7. The drug delivery device of claim 5 for oral drug delivery.

8. A bone cement comprising an unsaturated polyanhydride copolymer of aliphatic and aromatic dicarboxylic acids and a diacid selected from the group consisting of fumaric acid and 1,4-phenylenediacrylic acid having at least one double bond available for cross-linking, wherein said polyanhydride has a melting point of less than about 200° C. and a high degree of crystallinity and is soluble in organic solvents, wherein said bone cement is biodegradable and biocompatible.

9. A method for controlled drug delivery comprising providing an unsaturated biocompatible polyanhydride copolymer of aliphatic and aromatic dicarboxylic acids and a diacid selected from the group consisting of fumaric acid and 1,4-phenylenediacrylic acid having at least one double bond available for crosslinking, wherein said polyanhydride has a melting point of less than about 200° C. and a high degree of crystallinity and is soluble in organic solvents, and a bioactive compound.

10. The method of claim 9 further comprising encapsulating the bioactive compound within the polyanhydride.

11. The method of claim 10 further comprising crosslinking the polyanhydride.

12. The method of claim 11 wherein the polyanhydride is crosslinked with gamma irradition.

13. The method of claim 13 further comprising implanting the polyanhydride composition.

14. A method for repairing injuries to bone comprising providing an unsaturated polyanhydride copolymer of aliphatic and aromatic dicarboxylic acids and a diacid selected from the group consisting of fumaric acid and 1,4-phenylenediacrylic acid having at least one double bond available for crosslinking, wherein said polyanhydride has a melting point of less than about 200° C. and a high degree of crystallinity and is soluble in organic solvents, wherein said bone cement is biodegradable and biocompatible.

15. The method of claim 14 further comprising applying the unsaturated polyanhydride to a bone injury and cross-linking the polyanhydride.

* * * * *